United States Patent
Ha et al.

(10) Patent No.: US 9,815,046 B2
(45) Date of Patent: Nov. 14, 2017

(54) STORING METHOD OF ACTIVATED CATALYSTS FOR FISCHER-TROPSCH SYNTHESIS

(71) Applicant: KOREA RESEARCH INSTITUTE OF CHEMICAL TECHNOLOGY, Daejeon (KR)

(72) Inventors: Kyoung Su Ha, Daejeon (KR); Geun Jae Kwak, Daejeon (KR); Min Hee Woo, Gumi-si (KR); Yun Jo Lee, Daejeon (KR); Ki Won Jun, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/392,244

(22) PCT Filed: Nov. 26, 2014

(86) PCT No.: PCT/KR2014/011389
§ 371 (c)(1),
(2) Date: Dec. 24, 2015

(87) PCT Pub. No.: WO2015/080452
PCT Pub. Date: Jun. 4, 2015

(65) Prior Publication Data
US 2016/0296918 A1    Oct. 13, 2016

(30) Foreign Application Priority Data

Nov. 28, 2013  (KR) ........................ 10-2013-0146548

(51) Int. Cl.
| | |
|---|---|
| *B01J 23/89* | (2006.01) |
| *C10G 2/00* | (2006.01) |
| *C07C 1/04* | (2006.01) |
| *B01J 37/16* | (2006.01) |
| *B01J 37/02* | (2006.01) |
| *B01J 23/88* | (2006.01) |
| *B01J 21/12* | (2006.01) |
| *B01J 31/02* | (2006.01) |
| *B01J 31/26* | (2006.01) |

(52) U.S. Cl.
CPC .......... *B01J 23/8913* (2013.01); *B01J 21/12* (2013.01); *B01J 23/88* (2013.01); *B01J 31/02* (2013.01); *B01J 31/26* (2013.01); *B01J 37/0219* (2013.01); *B01J 37/16* (2013.01); *C07C 1/045* (2013.01); *C07C 1/0425* (2013.01); *C07C 1/0435* (2013.01); *C07C 1/0445* (2013.01); *C10G 2/333* (2013.01); *B01J 2231/625* (2013.01); *B01J 2531/005* (2013.01); *C07C 1/04* (2013.01); *C10G 2400/20* (2013.01); *C10G 2400/22* (2013.01); *Y02P 30/40* (2015.11)

(58) Field of Classification Search
None
See application file for complete search history.

(56) References Cited

U.S. PATENT DOCUMENTS

| | | | |
|---|---|---|---|
| 6,475,943 B1 | 11/2002 | Hoek et al. | |
| 2002/0156137 A1 | 10/2002 | Zhou et al. | |
| 2004/0127585 A1 | 7/2004 | Raje | |
| 2004/0259963 A1 | 12/2004 | Huang et al. | |
| 2005/0182145 A1* | 8/2005 | Mohedas | B01J 23/75 518/716 |
| 2006/0111232 A1* | 5/2006 | Spena | B01J 8/006 502/29 |
| 2011/0301024 A1 | 12/2011 | Terorde et al. | |

FOREIGN PATENT DOCUMENTS

| | | | |
|---|---|---|---|
| KR | 10-2011-0094462 A | 8/2011 | |
| KR | 10-2013-0102510 A | 9/2013 | |
| WO | 03/002252 A1 | 1/2003 | |
| WO | WO 2014144855 A2 * | 9/2014 | ............. B01J 38/50 |

OTHER PUBLICATIONS

Hammache et al., "Passivation of a Co—Ru/γ—Al$_2$O$_3$ Fischer-Tropsch catalyst," *Catalysis Today* 71:361-367 (2002).
Huber et al., "Remarks on the passivation of reduced Cu-, Ni-, Fe-, Co-based catalysts," *Catalysis Letters* 110(3-4):211-220 (Sep. 2006).

* cited by examiner

*Primary Examiner* — Medhanit Bahta
(74) *Attorney, Agent, or Firm* — Seed IP Law Group LLP

(57) ABSTRACT

The present invention relates to a method for producing the activated catalyst for Fischer-Tropsch synthesis comprising: a first step of reducing a catalyst for Fischer-Tropsch synthesis; a second step of preparing liquid hydrocarbon in which a part or all of molecular oxygen is eliminated; and a third step of introducing the reduced catalyst prepared in the first step into the liquid hydrocarbon prepared in the second step while blocking its contact with air. Since the reduced catalyst used for Fischer-Tropsch synthesis is introduced into liquid hydrocarbon from which molecular oxygen is removed or coated by liquid hydrocarbon, the catalyst for Fischer-Tropsch synthesis activated based on the present invention maintains a high activity even if exposed to the air for a long time, thereby easily facilitating the long-term storage and long-distance transfer of the reduced catalyst.

14 Claims, No Drawings

STORING METHOD OF ACTIVATED CATALYSTS FOR FISCHER-TROPSCH SYNTHESIS

TECHNICAL FIELD

The present invention relates to activated catalysts for Fischer-Tropsch synthesis which can be preserved for a long time while maintaining an activity of metal catalysts; a method thereof; and a method for producing liquid or solid hydrocarbon using said catalysts.

BACKGROUND ART

In 1923, Fischer and Tropsch, German chemists, developed a Fischer-Tropsch synthesis method (F-T synthesis method), and this method has enabled the production of liquid hydrocarbon from coal, natural gas, biomass and the like by way of syngas. A process producing liquid hydrocarbon from coal is referred to as a coal-to-liquid (CTL) process, a process producing from natural gas is referred to as a gas-to-liquid (GTL) process, and a process producing from biomass is referred to as a biomass-to-liquid (BTL) process, and recently, similar processes are collectively referred to as XTL ("X" resource-to-liquid) processes.

These processes first convert each resource material into syngas using methods such as gasification and reforming, and the composition of the syngas suited for XTL processes for producing liquid fuel preferably has a hydrogen-to-carbon monoxide ratio of approximately 2 as shown in the following Reaction Formula 1.

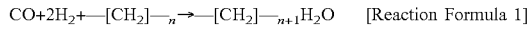

$$CO + 2H_2 + -[CH_2]-_n \rightarrow -[CH_2]-_{n+1} H_2O \quad \text{[Reaction Formula 1]}$$

(CO, $2H_2$, $-[CH_2]-_n$, and $H_2O$ represent carbon monoxide, hydrogen, hydrocarbon having chain length of n (number of carbons=n), and water, respectively.)

The ratio of hydrogen exceeding 2 is not preferable since it increases the selectivity on methane, and consequently, the selectivity on $C_{5+}$ (hydrocarbon having 5 or more carbon atoms) relatively decreases. In Reaction Formula 1, olefin and oxygenate (a molecule including oxygen atoms such as alcohol, aldehyde, carboxylic acid and ketone) are also produced as by-products in addition to hydrocarbon having linear chains as shown above.

One of the main purposes of XTL processes is to obtain liquid fuels, and therefore, the latest trend is to decrease the selectivity on methane and to produce linear hydrocarbon, in particular, $C_{5+}$ linear hydrocarbon with high selectivity by optimizing a selection of a reaction catalyst, a syngas ratio, a temperature, a pressure and the like. Herein, cobalt-series catalysts are normally used as the reaction catalyst, and such metal catalysts are used by being uniformly dispersed and supported on the surface of a support such as alumina, silica and titania. For the improvement of catalyst performances, noble metals such as Ru, Pt and Re may be used as a co-catalyst.

Such catalysts are normally used by being supported by a support such as alumina ($\gamma$-$AlO_3$, $\alpha$-$Al_2O_3$ and the like), silica ($SiO_2$), titania ($TiO_2$) and magnesia (MgO). However, the use of silica materials having mesoporous structures such as SBA-15 and MCM-41, and carbon-based materials having mesoporous structures such as CMK-3 and carbon nanotubes has also been expanded recently.

In general, an incipient wetness method, an impregnation method and the like are used for such supports when the catalysts are supported by the supports. For example, a target amount of the catalyst material is supported in the pores of the support while repeatedly performing processes of dissolving a cobalt salt of acid (Co $(NO_3)_2 \cdot 6H_2O$ and the like), which is a catalyst precursor, and a salt such as Pt, Ru and Re used as a co-catalyst in proper solvents to prepare a mixed solution of the precursor, and impregnating the mixed solution of the precursor in the pores of the support, followed by drying. Next, the dried catalyst goes through a calcination process under air or inert gas atmosphere, and catalyst particles having a form in which cobalt oxide crystals are supported in the support are obtained. A Fischer-Tropsch cobalt catalyst shows an activity in a reduced metal state, and therefore, the catalyst has to go through sufficient reduction processes before reaction in every possible way. In a laboratory-scale experiment for developing catalysts, an in situ reduction method, in which the temperature is raised up to a reduction temperature while flowing reducing gas with a calcinated catalyst to be filled into a reactor, is normally used. However, commercial reactors often employ other methods since reduction temperatures are generally much higher than reaction temperatures, and separate reducing gas injection equipment is required for an in situ reduction method.

In most commercial processes, reduction is carried out by supplying reducing gas (a mixture of hydrogen and an inert gas where the hydrogen content is approximately 5 to 10%) with additional catalyst reduction equipment. Cobalt metals in a reduced state violently react with oxygen in air and are oxidized again. Therefore, a proper treatment is necessary to not expose cobalt metals to air, or to minimize the degree of oxidation when exposed. Such a treatment is referred to as passivation, and by an intentional mild oxidation of the surface only through the supply of a mixed gas (normally consisting of oxygen and an inert gas) with a low concentration of oxygen, the activity of a catalyst can be minimally degraded when exposed to air during its transfer.

However, the passivation method has several problems. First, the degree of proper passivation is very difficult to identify. The degree of oxidation treatment required for minimizing violent oxidation during the air exposure is different for each catalyst. In addition, there are problems that initial activity is not satisfactory since oxidation has been partially progressed before use, and activity is generally low compared to an in situ reduction method.

In order to solve such problems, S. Hammache et al. (refer to S. Hammache, J. G. Goodwin, Jr., R. Oukaci, *Catalysis Today*, 2002, 71, 361-367) designed a passivation method using CO gas or (CO+$H_2$) gas. However, the method has a problem in that the activity of a catalyst is degraded due to the production of graphitic carbon on the surface of the catalyst, and additionally, the method further requires a heating equipment capable of being operated at high temperatures in a reactor since the reduction process includes treating the catalyst with hydrogen gas for 10 hours at a high temperature of 350° C. when activating a carbide compound catalyst.

In addition, F. Huber et al. (refer to F. Huber, H. Venvik, *Catalysis Letters*, 2006, 3-4, 211-220) proposed an encapsulation method using organic materials, a carbon layer coating method, a method of passivating metal catalysts through oxygen and $N_2O$ treatments. However, for activating, the method also requires reduction conditions of heating for 16 hours at a high temperature of 350° C. while supplying hydrogen gas.

Furthermore, various passivation methods carried out through the production of carbide and carbon have also been proposed. WO 03/002252 discloses a method for transferring or activating a catalyst by passivating the activated catalyst using a method of coating the surface of a metal precursor material supported in a support with carbon by adding a certain amount (5 to 20%) of short-chained hydrocarbon (methane, ethane, etc.) together with hydrogen gas, or introducing a syngas, in order to produce a carbide form of a metal catalyst in a hydrogen reduction process.

The metal catalysts having a carbide form are known to have increased activity after activation, and the activity is known to be further improved when a metal carbide form is formed in certain parts of an activated metal catalyst. However, WO 03/002252 discloses that hydrogen reduction treatment at a high temperature of 350° C. or greater is necessary to activate the catalyst passivated in a metal carbide form, thus requiring additional activation equipment in addition to the reaction equipment.

Meanwhile, even when an ex situ reduction method is used, a method without passivation by oxygen, that is, a method of introducing a catalyst directly into a reactor without being exposed to oxygen at all may be considered. However, the method also has problems. Catalyst reduction equipment and a reactor need to be relatively close, and the equipment may become larger since gas supply equipment, power, a heater and the like required for reduction all need to be included in a reactor system. In addition, there is a new challenging task on how to transfer solid particles from the catalyst reduction equipment to the reactor.

In order to solve these problems, Sasol Limited and the like have devised and used methods in which, by coating a reduced catalyst with wax or introducing the reduced catalyst inside a wax material, the transfer of the catalyst becomes simple while capable of blocking its contact with air (U.S. Patent Application Publication No. 2011/0301024). However, because wax materials are solid at room temperature, they need to be liquidified by heating in order to coat or insert catalyst particles, thus making the process complicated.

DISCLOSURE OF INVENTION

Technical Problem

Under such background, the present inventors have tried to develop a new storing method for maintaining a long-term activation of the metal catalyst which is activated by reducing gas, while overcoming limitations on an existing method for activating the metal catalyst for Fischer-Tropsch synthesis.

Technical Solution

A first aspect of the present invention is to provide a method for producing the activated catalyst for Fischer-Tropsch synthesis comprising a first step of reducing a catalyst for Fischer-Tropsch synthesis; a second step of preparing liquid hydrocarbon in which a part or all of molecular oxygen is eliminated; and a third step of introducing the reduced catalyst prepared in the first step into the liquid hydrocarbon prepared in the second step while blocking its contact with air.

A second aspect of the present invention is to provide a method for producing liquid or solid hydrocarbon using a Fischer-Tropsch synthesis reaction. The method includes a step a of preparing the catalyst for Fischer-Tropsch synthesis activated by the method disclosed in the first aspect of the present invention; a step b of applying the catalyst for Fischer-Tropsch synthesis, which was activated by the step a, to a Fischer-Tropsch synthesis reactor; and a step c of carrying out the Fischer-Tropsch synthesis reaction using the activated catalyst.

A third aspect of the present invention is to provide the catalyst for Fischer-Tropsch synthesis activated by the method disclosed in the first aspect of the present invention, wherein the reduced metal catalyst used for Fischer-Tropsch synthesis is immersed in or coated by liquid hydrocarbon.

Hereinafter, the present invention will be described in detail.

Although there is a preservation method for introducing the reduced metal catalyst particles inside the wax as a way of maintaining the activity of the metal catalyst activated by the reduced gas for a long time, the process becomes complicated because wax materials are solid at room temperature which means that they need to be liquefied by heating in order to coat or immerse the catalyst particles. The method for introducing the reduced metal catalyst particles into wax and preserving the particles is the relatively easy to be applied to a slurry reactor. However, additional heating and separating equipment for eliminating wax need to be prepared before introducing into the reactor in the case of a tube type fixed-bed reactor where an exact volume of the catalyst should be placed in the tube with diluents (i.e. alumina) in a consistent ratio (Experimental Example 1). Further, because both transfer and the following introducing into the reactor are also problematic, the applicability reduces on-site.

In order to recognize and solve the problems about wax, and to preserve the activity of the metal catalysts activated by hydrogen-containing gas or corresponding reduced gas for a long time, the present invention stores and transfers the activated metal catalyst for Fischer-Tropsch synthesis by liquid hydrocarbon in which molecular oxygen molecules are deaerated.

Outstanding switching performances and selectivity were observed even if the catalyst was transferred by production facilities from a relatively long distance because high activity can be maintained for a long time when using the storing method of the present invention. Further, it is advantageous that only a small amount of liquid hydrocarbon is necessary since the method involves coating the powdery catalyst particles with liquid hydrocarbon. In addition to this, the catalyst preserved in liquid hydrocarbon can easily be isolated from liquid hydrocarbon using a Büchner funnel, filter paper, and aspirators inside the reactor even shortly before filling the catalyst. In real production sites, considering the amount of the catalyst, the equipment functioning like the above-described equipment can be used instead. Furthermore, because liquid hydrocarbon, which coats or immerses the metal catalysts activated by the present invention, is liquid at room temperature, the exact amount of activated catalysts can be placed in the tube type fixed-bed reactor wherein the exact amount of the catalysts should be placed while liquid hydrocarbon is eliminated without any additional heating process.

A method for producing the activated catalyst for Fischer-Tropsch synthesis prepared in the first aspect of the present invention comprises a first step of reducing the catalyst for Fischer-Tropsch synthesis using hydrogen or carbon monoxide-containing reduced gas; a second step of preparing liquid hydrocarbon in which a part or all of molecular oxygen is eliminated; and a third step of introducing the reduced catalyst prepared in the first into liquid hydrocarbon prepared in the second step while blocking its contact with air.

In the present invention, the catalyst for Fischer-Tropsch synthesis is the reacting catalyst, and cobalt-series or iron-series of the catalysts are mainly used. Further, they may be supported by a support such as silica, alumina, titania, zeolite, a mesopore carbon structure, a carbon nanotube, mesopore silica, a silica/alumina mixture, a titania/silica mixture and an alumina/titania mixture. In addition to this, the metal-containing catalyst for Fischer-Tropsch synthesis may further include co-catalyst metals such as platinum (Pt), palladium (Pd), rhodium (Rh), ruthenium (Ru) and renium (Re).

The catalyst for Fischer-Tropsch synthesis in the present invention may include dried catalysts, calcinated catalysts, reduced catalysts and catalysts of which activity is degraded by being used in a Fischer-Tropsch synthesis reaction as described below.

The "dried catalyst" may include a catalyst in a dried state after supporting catalyst and/or co-catalyst precursors in a support using catalyst preparation methods such as an incipient wetness impregnation method, an impregnation method, a coprecipitation method, a sol-gel method, a chemical deposition method, a plasma method or a deposition-precipitation method. Then, the dried catalyst goes through a calcination process for producing metal oxide crystals inside the pores of the support, and the calcination may be progressed in air or an inert gas atmosphere (for example, gases that are not reactive such as nitrogen, helium and argon), and a catalyst after calcination refers to the "calcinated catalyst". The metal oxide crystals of the calcinated catalyst are reduced to metals using a reducing gas such as hydrogen in order to be used in Fischer-Tropsch synthesis, and the state is designated as the "reduced catalyst."

Meanwhile, the catalysts used in syngas-using hydrocarbon synthesis reactions show catalyst deactivation by 5 to 10% after long-time reactions (200 hours or more). The reasons for the deactivation of the used catalysts are mainly due to the influences of active site degradation due to wax, a product produced during the reaction, oxidation of a metal catalyst due to the water produced, and blockage of pores due to carbon deposition rather than the influences of catalyst breakage or catalyst poison. The deactivated catalysts from the syngas-using hydrocarbon synthesis reactions can be reduced to metal and regenerated by treating with hydrogen-containing gas.

For example, the mixed solution, wherein the metal precursors of the cobalt precursors (Co $(NO_3)_2 \cdot 6H_2O$) are dissolved in solvents such as water and ethanol, is introduced into pores of the multiple porous oxide supports including silica and alumina by the impregnation method and the like. The activity or selectivity can be enhanced using a small amount of noble material co-catalysts such as platinum (Pt), ruthenium (Ru), and renium (Re). More metal input can be added if insufficient, and if necessary, additional metal precursor solution can be introduced after drying and calcination. After introducing a sufficient amount of metal precursor solution, the catalyst particles are produced in the form in which metal oxide crystals are dispersed in the supports after drying and calcination. Although the above-described examples are about an explanation of the incipient wetness impregnation method in which the cobalt precursor solution is supported in the supports, the catalysts can be produced after placing catalysts or co-catalysts in the supports by the catalyst preparation methods such as a solution impregnation method, a co-precipitation method, a sol-gel method, a chemical deposition method, a plasma method, or a deposition-precipitation method.

The first step, which reduces the catalyst for Fischer-Tropsch synthesis using hydrogen or carbon monoxide-containing reducing gas according to the first aspect of the present invention, is a step for forming the catalyst for Fischer-Tropsch synthesis in which a part or all of the metal oxides in the metal oxide-containing catalysts for Fischer-Tropsch synthesis are reduced to metals.

In order to be used for the Fischer-Tropsch synthetic reaction, a process of reducing and activating the metal oxide crystals is definitely required.

The reduced gases required for the process are mixed gases containing a fixed quantity of hydrogen, mixed gas containing a fixed quantity of carbon monoxide, or mixed gas containing a fixed quantity of both hydrogen and carbon monoxide, and the process is carried out at a reducing temperature ranging from 300° C. to 500° C.

The reduced gas can be used in combination with the inert gas. Being treated with carbon monoxide, the inert gas may function as a carrier gas facilitating the movement of hydrogen or carbon monoxide, and also function to adjust the concentration. An explanation on the inert gas is described later.

Herein, the catalyst for Fischer-Tropsch synthesis in which a part or all of the metal oxides in the metal oxide-containing catalyst for Fischer-Tropsch synthesis are reduced to metals may be obtained by:

(1) reducing the metal oxides with hydrogen at high temperatures;

(2) partly reducing the metal oxides to metals by treating the calcinated catalyst obtained after calcination with a gas mixture including carbon monoxide in 5 to 100% under an atmosphere of 5 bar or greater, and at a temperature of 300° C. to 450° C.; or (3) partly reducing the metal oxides to metals by treating the dried catalyst, which is obtained after supporting the catalyst precursor using methods such as impregnation and then drying, with a gas mixture including carbon monoxide in 5 to 100% at a temperature of 300° C. to 450° C.

In the cases of (2) and (3), some may be carbidized immediately after being reduced to metals. The metal carbide-containing catalyst for Fischer-Tropsch synthesis can be reduced to metals under mild conditions such as the Fischer-Tropsch synthesis reaction temperature after filling the Fischer-Tropsch synthesis reactor. When a cobalt catalyst is used, the Fischer-Tropsch synthesis reaction temperature normally ranges from 200° C. to 300° C.

Because the catalyst reduced and activated in the first step of the first aspect of present invention react with oxygen aggressively, cobalt metal become rapidly oxidized if merely taken out in air, thereby transforming rapidly into the metal oxides in the form of CoO or $Co_3O_4$. Herein, heat is produced severely from an aggressive oxidation and an oxidation process is accelerated.

Therefore, blocking air contact can be used as one of the methods to maintain an activated state, but in the present invention, liquid hydrocarbon may be used to block the contact with air. It is preferable to have a part or all of molecular oxygen is eliminated in the above-described liquid hydrocarbon.

As far as usable liquid hydrocarbon is concerned, saturated or unsaturated hydrocarbon which has 5 or more carbons can be used. Among these hydrocarbons, one or more than two liquid hydrocarbon can be mixed together and used. An example of liquid hydrocarbon can be squalane ($C_{30}H_{62}$).

Further, the second step of preparing hydrocarbon in which a part or all of molecular oxygen is eliminated according to the first aspect of the present invention may involve eliminating molecular oxygen by bubbling the inert gas in liquid hydrocarbon for more than 12 hours, preferably for more than 24 hours.

Herein, the inert gas refers to the gas that is inert in the reduced Fischer-Tropsch catalyst, and for example, any gases that do not re-oxidize the reduced metal catalyst can be used. Non-limited examples include nitrogen, neon, helium, argon, krypton, xeon, radon, and a mixture of these elements, and using a mixture of two or more elements in a random ratio is also possible.

The third step based on the first aspect of the present invention is a step of introducing the reduced catalyst prepared in the first step into the hydrocarbon prepared in the second step without air contact.

The amount of hydrocarbon such as squalane is sufficient as long as the catalyst particles are soaked enough in squalane to coat the surface, and more specifically, the volume that is 0.5 or 1.5 times more than the appearing volume of the catalyst is enough.

According to one embodiment of the present invention, the catalyst introduced inside squalane can be prepared after eliminating more than 50% of molecular oxygen in liquid by bubbling squalane with the inert gas such as argon, helium, and nitrogen, and introducing the reduced catalyst particles herein without contacting air. When pouring the reduced catalyst particles into a container of squalane, the catalyst should not be in contact with air upon its insertion by pushing air in the upper container after blowing a sufficient amount of the inert gas into the container.

When the catalyst reduction equipment is connected to the container of squalane by a tube or a pipe, the inert gas is continuously blown into the container, and the equipment is designed to discharge the inert gas into a suitable spot in the container, the activated catalysts can be introduced into squalane smoothly without air contact. Herein, an explanation on the inert gas was same as before.

A method for producing the activated catalyst for Fischer-Tropsch synthesis can be applied to most catalysts which can only be used after being reduced, and the method is also included in the scope of the present invention.

The catalyst for Fischer-Tropsch synthesis activated by the method disclosed in the first aspect of the present invention may be in slurry form or liquid form. The catalyst may be the reduced metal catalyst for Fischer-Tropsch synthesis immersed in liquid hydrocarbon or coated by liquid hydrocarbon.

Meanwhile, a method for producing liquid or solid hydrocarbon using the Fischer-Tropsch synthesis reaction based on the second aspect of the present invention comprises a step a of preparing the catalyst for Fischer-Tropsch synthesis activated by the method disclosed in the first aspect of the present invention; a step b of applying the catalyst for Fischer-Tropsch synthesis, which was activated by the step a, to the Fischer-Tropsch synthesis reactor; and a step c of carrying out the Fischer-Tropsch synthesis reaction using the activated catalyst.

Further, a step of collecting and storing the catalyst for Fischer-Tropsch synthesis that have been activated after the step a may additionally be included.

In the present invention, the above-described reactors may be a slurry reactor, a fixed-bed reactor, a multiplex channel reactor, or a continuous stirred tank reactor. Specifically, because the catalyst for Fischer-Tropsch synthesis activated by the method disclosed in the present invention are the reduced metal catalyst which are immersed in liquid hydrocarbon or coated by liquid hydrocarbon, the exact amount of the activated catalysts can be placed in the tube type fixed-bed reactor wherein the exact amount of the catalysts should be placed while liquid hydrocarbon is eliminated without any additional heating process.

The Fischer-Tropsch synthesis reaction may be carried out at a reaction temperature of 200° C. to 350° C. (preferably 200° C. to 240° C.), a reaction pressure of 5 to 30 kg/cm$^3$ (preferably 1.0 to 2.5 MPa), and a space velocity of 1,000 to 12,000 h$^{-1}$ (preferably 2,000 to 10,000 h$^{-1}$), however, the reaction conditions are not limited thereto. In addition, the Fischer-Tropsch synthesis reaction is preferably carried out while maintaining the hydrogen/carbon monoxide reaction ratio at a molar ratio of 1 to 2.

In addition, the method for preparing hydrocarbon according to the present invention may further include a reforming reaction step of Fischer-Tropsch synthesis reaction products after the step c.

Advantageous Effects

The present invention enables a long-term preservation and prevents the loss of activity during a long-distance transfer by introducing the activated metal catalysts from Fischer-Tropsch synthesis into liquid hydrocarbon in which molecular oxygen is deaerated. Further, the process is much easier than a method for cutting, splitting, and introducing catalytic mass solidified by the introduction inside wax and the like because the catalysts in slurry form or in the liquid filtration form can be directly introduced into the reactor upon the introduction at production sites. In addition to this, additional activation for the catalyst is not required at the production sites and therefore, activating apparatus is also not required because the catalyst for Fischer-Tropsch synthesis is preserved after activation.

BEST MODE FOR CARRYING OUT THE INVENTION

Hereinafter, the present invention will be described in details with reference to the following examples. However, these examples are for illustrative purposes only, and the scope of the present invention is not limited to these examples.

An excellence of the present invention is proven by a comparison and review between the present invention and the preservation method using molecular oxygen in the Examples below.

Example 1: A Preservation Method for the Reduced Catalyst Using Liquid Hydrocarbon A catalyst having a composition of 0.05Pt-24Co/1.5Si/alumina (numbers in front of the elements represent the mass ratios of the corresponding elements included in the catalyst particles) was prepared by impregnation, and subsequently, the catalyst was dried for 12 hours at 110° C. and calcinated for 5 hours at 400° C. Next, 0.3 g of the calcinated catalyst was filled in the reactor, and reduced under atmospheric pressure for 5 hours at 400° C. using 80 sscm of hydrogen-containing gas (5% $H_2$/He).

Squalane ($C_{30}H_{62}$), a type of liquid hydrocarbon, was bubbled with Argon for 24 hours while eliminating molecular oxygen in the liquid. When pouring the reduced catalyst particles into a container of squalane, the catalyst should not be in contact with air upon its introduction by pushing air in the upper container after blowing a sufficient amount of the inert gas into the container. Next, the container of squalane remained open in air at room temperature for 1 week for air to move in and out of the container.

Comparative Example 1: A Preservation Method for the Catalyst by the Passivation Method Using Molecular Oxygen Comparative Example 1-1: Passivation Method Using 1 Volume % Oxygen (The Rest of Nitrogen)

As shown in Example 1, the reduced catalyst was cooled down to room temperature and passivated by flowing 1 volume % oxygen-containing liquid mixture (the rest of nitrogen) for 1 hour. Next, the catalysts was taken out of the reactor and placed in air at room temperature for 1 week.

Comparative Example 1-2: Passivation Method Using 5 Volume % Oxygen (The Rest of Nitrogen)

Except for the fact that the oxygen content is 5 volume %, the process was carried out in the same manner as Comparative Example 1-1.

Comparative Example 1-3: Passivation Process Using 10 Volume % Oxygen (The Rest of Nitrogen)

Except for the fact that the oxygen content is 10 volume %, the process was carried out in the same manner as Comparative Example 1-1.

Experimental Example 1: Fischer-Tropsch Synthesis Reaction

Conversion ratios and selectivity were confirmed by carrying out the Fischer-Tropsch synthesis reaction, wherein the activated catalyst prepared in the Examples and the Comparative Examples were introduced into the Fischer-Tropsch synthesis reactor.

The reactor used in the experiments was a tube type fixed-bed reactor, wherein the pipe has a diameter of 9.525 mm and a catalyst amount of 0.3 g, the ratio of the catalyst and a diluent was 1:5 (weight ratio), the size of the catalyst ranged from 50 to 150 μm, and the diluent (α-alumina) having a similar size to the catalyst was used. A reaction temperature ranged from 220 to 230° C., a reaction pressure was 2.0 MPa, and a space velocity was 4,000 mL syngas/g-cat/h, and a syngas composition of $H_2/CO/CO_2/Ar=57.3/28.4/9.3/5$ was used.

1) Result of the Fischer-Tropsch Synthesis Reaction of the Activated Catalyst in Example 1

The activated catalyst preserved in squalane for 1 week based on Example 1, was isolated from squalane using the Büchner funnel, filter paper, and aspirators. The Fischer-Tropsche synthesis reaction was carried out by introducing the tube type micro-fixed-bed reactor. The results are shown in Table 1 below.

TABLE 1

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 74.40 | 4.79 | 6.23 | 88.98 |
| 230 | 4000 | 88.98 | 5.74 | 6.66 | 87.59 |

2) Result of the Fischer-Tropsch Synthesis Reaction of the Activated Catalyst in Comparative Example 1-1

The Fischer-Tropsch synthesis reaction was carried out using the activated catalyst, which was preserved for 1 week based on Example 1-1. The results are shown in Table 2 below.

TABLE 2

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 61.10 | 4.95 | 5.48 | 89.57 |
| 230 | 4000 | 77.23 | 5.20 | 5.66 | 89.13 |

3) Result of the Fischer-Tropsch Synthesis Reaction of the Activated Catalyst in Comparative Example 1-2

The Fischer-Tropsch synthesis reaction was carried out using the activated catalyst, which was preserved for 1 week based on Example 1-2. The results are shown in Table 3 below.

TABLE 3

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 60.92 | 6.12 | 6.96 | 86.92 |
| 230 | 4000 | 79.14 | 6.44 | 7.04 | 86.52 |

4) Result of the Fischer-Tropsch Synthesis Reaction of the Activated Catalyst in Comparative Example 1-3

Fischer-Tropsch synthesis reaction was carried out using the activated catalyst, which was preserved for 1 week based on Example 1-3. The results are shown in Table 4 below.

TABLE 4

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 62.85 | 6.02 | 6.93 | 87.05 |
| 230 | 4000 | 81.03 | 6.41 | 7.19 | 86.40 |

The activated catalysts based on Example 1, even after being exposed to air for 1 week, the conversion ratio was 11.55 to 13.48% higher at a temperature of 220° C. and the ratio was 7.95 to 11.75% higher at a temperature of 230° C. during the Fischer-Tropsch synthesis reaction. Therefore, it was confirmed that the activity of the reduced metal catalyst preserved based on the present invention was much higher compared to the activity of the catalyst preserved based on the passivation method using molecular oxygen. In both cases, the selectivity on hydrocarbon did not show a significant difference.

The invention claimed is:

1. A method for producing an activated catalyst for Fischer-Tropsch synthesis comprising:
   a first step of reducing a catalyst for Fischer-Tropsch synthesis using hydrogen or carbon monoxide-containing reduced gas;
   a second step of eliminating molecular oxygen by bubbling an inert gas in liquid hydrocarbon for more than 12 hours to prepare liquid hydrocarbon in which a part or all of molecular oxygen is eliminated, wherein the liquid hydrocarbon is a saturated or unsaturated hydrocarbon having 5 or more carbons, and the liquid hydrocarbon is a liquid at room temperature;
   a third step of introducing the reduced catalyst prepared in the first step into the liquid hydrocarbon prepared in the second step without contacting the catalyst with air to prepare a coated catalyst particle with the liquid hydrocarbon; and
   a fourth step of isolating the coated catalyst particle prepared in the third step from the liquid hydrocarbon.

2. The method for producing the activated catalyst according to claim 1, wherein the first step is carried out at a temperature ranging from 300 to 500° C.

3. The method for producing the activated catalyst according to claim 1, wherein the inert gas is inert to the reduced catalyst.

4. The method for producing the activated catalyst according to claim 1, wherein the inert gas is selected from the group consisting of nitrogen, neon, helium, argon, krypton, xeon, radon, and a mixture thereof.

5. The method for producing the activated catalyst according to claim 1, wherein the liquid hydrocarbon is squalane.

6. The method for producing the activated catalyst according to claim 1, wherein the inert gas is bubbled for more than 24 hours to eliminate molecular oxygen in the liquid hydrocarbon.

7. The method for producing the activated catalyst according to claim 1, wherein the catalyst comprises cobalt or iron as an active ingredient.

8. The method for producing the activated catalyst according to claim 1, wherein the catalyst is supported by any one support selected from the group consisting of silica, alumina, titania, zeolite, a mesopore carbon structure, a carbon nanotube, mesopore silica, a silica/alumina mixture, a titania/silica mixture and an alumina/titania mixture.

9. The method for producing the activated catalyst according to claim 7, wherein the catalyst containing the metal further comprises one or more co-catalyst metals selected from the group consisting of platinum (Pt), palladium (Pd), rhodium (Rh), ruthenium (Ru) and rhenium (Re).

10. A method for preparing liquid or solid hydrocarbon using a Fischer-Tropsch synthesis reaction comprising:
    step a) activating a catalyst for Fischer-Tropsch synthesis according to claim 1 to generate an activated catalyst;
    step b) applying the activated catalyst to a Fischer-Tropsch synthesis reactor; and
    step c) carrying out the Fischer Tropsch synthesis reaction using the activated catalyst.

11. The method of claim 10, wherein the Fischer-Tropsch synthesis reaction is carried out at a temperature ranging from 200 to 300° C.

12. The method of claim 10, wherein the Fischer-Tropsch synthesis reactor is a tube type fixed-bed reactor.

13. The method of claim 10 further comprising a step of collecting and storing the activated catalyst after step a).

14. The method of claim 10, wherein the catalyst is activated by reducing at a temperature ranging from 300 to 500° C.

* * * * *